US008933809B2

(12) United States Patent
Kanemitsu et al.

(10) Patent No.: US 8,933,809 B2
(45) Date of Patent: Jan. 13, 2015

(54) SLEEP EVALUATION DEVICE AND DISPLAY METHOD FOR SLEEP EVALUATION DEVICE

(75) Inventors: Yoko Kanemitsu, Ibaraki (JP); Yasuko Emori, Kyoto (JP); Feilang Tseng, Kyoto (JP); Masakazu Tsutsumi, Kyoto (JP); Toshiro Ito, Toki (JP); Noboru Shinomiya, Mishima-gun (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 13/982,421

(22) PCT Filed: Nov. 15, 2011

(86) PCT No.: PCT/JP2011/076264
§ 371 (c)(1),
(2), (4) Date: Jul. 29, 2013

(87) PCT Pub. No.: WO2012/114588
PCT Pub. Date: Aug. 30, 2012

(65) Prior Publication Data
US 2013/0310712 A1 Nov. 21, 2013

(30) Foreign Application Priority Data
Feb. 22, 2011 (JP) .................................. 2011-035705

(51) Int. Cl.
*G08B 23/00* (2006.01)
*A61B 5/00* (2006.01)
(Continued)

(52) U.S. Cl.
CPC ................ *A61B 5/4806* (2013.01); *A61B 5/11* (2013.01); *A61B 5/4809* (2013.01); *A61B 5/002* (2013.01); *A61B 5/6887* (2013.01); *A61B 5/742* (2013.01); *A61B 5/113* (2013.01); *A61B 5/4815* (2013.01)
USPC .......................................... 340/575; 600/595

(58) Field of Classification Search
USPC .......................................... 600/595; 340/575
See application file for complete search history.

(56) References Cited

U.S. PATENT DOCUMENTS

| 2007/0156060 A1* | 7/2007 | Cervantes ..................... 600/534 |
| 2008/0004811 A1 | 1/2008 | Suzuki et al. |
| 2009/0171165 A1* | 7/2009 | Izumi ............................. 600/300 |

FOREIGN PATENT DOCUMENTS

| CN | A-101467881 | 7/2009 |
| JP | A-2005-152310 | 6/2005 |

(Continued)

OTHER PUBLICATIONS

Feb. 21, 2012 International Search Report was issued in International Application No. PCT/JP2011/076264 (with translation).

(Continued)

*Primary Examiner* — Max Hindenburg
*Assistant Examiner* — Renee Danega
(74) *Attorney, Agent, or Firm* — Oliff PLC

(57) ABSTRACT

A measurement device is provided with a sensor for detecting body motion of a subject and a CPU for executing processing for generating display data. The CPU includes a first discrimination unit for discriminating a sleeping state of the subject for each unit period, based on a sensor signal output from the sensor, a second discrimination unit for discriminating a level of the sleeping state of a predetermined period consisting of a predetermined number of continuous unit periods, based on the sleeping state for each unit period, a decision unit for deciding a display mode for each predetermined period, according to the level of the sleeping state of the predetermined period, and a generation unit for generating display data for displaying the level of the sleeping state of the subject in the predetermined period on a display device with a graph along the time axis.

8 Claims, 18 Drawing Sheets

(51) Int. Cl.
*A61B 5/11* (2006.01)
*A61B 5/113* (2006.01)

(56) References Cited

FOREIGN PATENT DOCUMENTS

| JP | A-2005-237570 | 9/2005 |
| JP | A-2008-6005 | 1/2008 |
| JP | A-2008-142238 | 6/2008 |
| JP | A-2009-160001 | 7/2009 |

OTHER PUBLICATIONS

Sep. 3, 2014 Office Action issued in Chinese Patent Application No. 201180068312.0 (with English translation).

\* cited by examiner

| t1 | t2 | t3 | t4 | t5 | t6 | t7 | t8 | t9 | t10 | t11 | t12 | t13 | t14 | t15 | ... |
|----|----|----|----|----|----|----|----|----|-----|-----|-----|-----|-----|-----|-----|
| S | S | S | S | S | S | W | S | S | S | W | W | S | W | W | ... |

FIG. 9A

| t1 | t2 | t3 | t4 | t5 | t6 | t7 | t8 | t9 | t10 | t11 | t12 | t13 | t14 | t15 | ... |
|----|----|----|----|----|----|----|----|----|-----|-----|-----|-----|-----|-----|-----|
| S | S | S | S | S | S | S | S | S | S | W | W | W | W | W | ... |

FIG. 9B

| T1 | T2 | T3 | ... |
|----|----|----|-----|
| Lv1 | Lv1 | Lv2 | ... |

| DATE | | BED TIME | NIGHTTIME FROM PREVIOUS DAY | | | | | | MORNING | | | | | | DAYTIME | | | | WAKE UP TIME | SLEEPING HRS | MID-SLEEP WAKING TIME | |
|---|---|---|---|---|---|---|---|---|---|---|---|---|---|---|---|---|---|---|---|---|---|---|---|
| | | | 20 | 21 | 22 | 23 | 24 | 1 | 2 | 3 | 4 | 5 | 6 | 7 | 8 | 9 | 10 | 11 | 12 | 13 | | | FREQ | MIN |
| 1 | MON | 2:36 | | | | | | | | | | | | | | | | | | | 10:26 | 7:01 | 7 | 29 |
| 2 | TUES | 3:25 | | | | | | | | | | | | | | | | | | | 8:15 | 4:09 | 7 | 23 |
| 3 | WED | 1:41 | | | | | | | | | | | | | | | | | | | 9:59 | 6:48:00 | 6 | 60 |
| 4 | THU | 2:07 | | | | | | | | | | | | | | | | | | | 8:04 | 5:35 | 3 | 13 |
| 5 | FRI | 1:36 | | | | | | | | | | | | | | | | | | | 7:30 | 4:46 | 9 | 48 |
| 6 | SAT | 1:41 | | | | | | | | | | | | | | | | | | | 12:10 | 8:43 | 12 | 60 |
| 7 | SUN | 3:07 | | | | | | | | | | | | | | | | | | | 11:10 | 6:12 | 10 | 67 |
| ## | TUES | 1:26 | | | | | | | | | | | | | | | | | | | 9:09 | 5:46 | 8 | 79 |
| ## | WED | 2:29 | | | | | | | | | | | | | | | | | | | 8:36 | 4:23 | 6 | 78 |

FIG. 11

| DATE | | BED TIME | NIGHTTIME FROM PREVIOUS DAY | | | | | | | | | MORNING | | | | | | DAYTIME | | | | WAKE UP TIME | SLEEPING HRS |
|---|---|---|---|---|---|---|---|---|---|---|---|---|---|---|---|---|---|---|---|---|---|---|---|
| | | | 20 | 21 | 22 | 23 | 24 | 1 | 2 | 3 | 4 | 5 | 6 | 7 | 8 | 9 | 10 | 11 | 12 | 13 | | |
| 1 | MON | 2:36 | | | | | | | | | | | | | | | | | | | 10:26 | 7:01 |
| 2 | TUES | 3:25 | | | | | | | | | | | | | | | | | | | 8:15 | 4:09 |
| 3 | WED | 1:41 | | | | | | | | | | | | | | | | | | | 9:59 | 6:48 |
| 4 | THU | 2:07 | | | | | | | | | | | | | | | | | | | 8:04 | 5:35 |
| 5 | FRI | 1:36 | | | | | | | | | | | | | | | | | | | 7:30 | 4:46 |
| 6 | SAT | 1:41 | | | | | | | | | | | | | | | | | | | 12:10 | 8:43 |
| 7 | SUN | 3:07 | | | | | | | | | | | | | | | | | | | 11:10 | 6:12 |
| 8 | MON | | | | | | | | | | | | | | | | | | | | | |
| 9 | TUES | 1:26 | | | | | | | | | | | | | | | | | | | 9:09 | 5:46 |
| 10 | WED | 2:29 | | | | | | | | | | | | | | | | | | | 8:36 | 4:23 |
| 11 | THU | 2:01 | | | | | | | | | | | | | | | | | | | 7:33 | 4:01 |

SLEEP EVALUATION DEVICE AND DISPLAY METHOD FOR SLEEP EVALUATION DEVICE

TECHNICAL FIELD

The invention relates to sleep evaluation devices and display methods for sleep evaluation devices, and more particularly to a sleep evaluation device that evaluates the sleeping state of the person being evaluated in a non-invasive manner and a display method for the sleep evaluation device.

BACKGROUND ART

Sleep is an important element in staying healthy, and being aware of one's sleep patterns is important from the viewpoint of maintaining good health.

Polysomnography (PSG) is a typical method of measuring sleep patterns. Polysomnography is one method of examination used to diagnose sleep disorders, and involves measuring the brainwaves of the person being evaluated, and checking the depth of sleep based on changes in the brainwaves.

A simple method involves measuring temporal changes in the body motion of the person being evaluated using sensors that are arranged under the bedding, and judging the state and quality of sleep of the person being evaluated based on the measurement results, as disclosed in JP 2009-160001A (hereinafter, Patent Literature 1) and JP 2008-142238A (hereinafter, Patent Literature 2), for example.

CITATION LIST

Patent Literature

Patent Literature 1: JP 2009-160001A
Patent Literature 1: JP 2008-142238A

SUMMARY OF INVENTION

Technical Problem

However, there is a problem with polysomnography in that a significant burden is placed on the person being evaluated not only because electrodes and numerous sensors need to be attached to his or her head, but also because the person being evaluated has to wait while the examination is being carried out.

On the other hand, although the methods disclosed in Patent Literatures 1 and 2 arguably place a smaller burden on the person being evaluated than polysomnography since the invasiveness to the person being evaluated is lower than with polysomnography, there was a problem in that since sensors arranged under the bedding are used, restrictions are placed on the type of bedding, and, in the end, the burden on the person being evaluated remains to some extent.

Furthermore, with the methods disclosed in Patent Literatures 1 and 2, since a result is output after only discriminating between the sleeping state and the waking state, there was a problem in that a user who does not have specialist knowledge would have difficulty interpreting the sleeping state.

The present invention was made in consideration of such problems, and has as one object to provide a sleep evaluation device and a display method for the sleep evaluation device that are able to ease the burden on the person being evaluated and to present levels of the sleeping state of the person being evaluated in an easily understandable manner.

Solution to Problem

In order to attain the above object according to an aspect of the present invention, a sleep evaluation device includes a body motion detection unit that detects body motion of a subject, and an arithmetic operation unit that generates display data for displaying a level of a sleeping state of the subject in a predetermined period on a display device with a graph along a time axis, based on a detection result of the body motion detection unit. The arithmetic operation unit includes a first discrimination unit that discriminates the sleeping state of the subject for each unit period, based on the detection result of the body motion detection unit, a second discrimination unit discriminates the level of the sleeping state of the predetermined period which consists of a predetermined number of continuous unit periods, based on the sleeping state for each unit period discriminated by the first discrimination unit, a decision unit that decides a display mode for each predetermined period, according to the level of the sleeping state of the predetermined period, and a generation unit that generates display data that represents the level of the sleeping state of the predetermined period with the display mode.

Preferably, the display data is data for displaying segments representing the predetermined period continuously along the time axis, and the decision unit decides the display mode of the segments representing the predetermined period, according to the level of the sleeping state of the predetermined period.

More preferably, the decision unit decides a color that depends on the level of the sleeping state, as a color of the segments representing the predetermined period.

More preferably, the display data is data for displaying the segments representing the predetermined period continuously along the time axis, with respect to an axis representing the level of the sleeping state that is orthogonal to the time axis, and the decision unit decides a position that depend on the level of the sleeping state, as a display position in a direction of the axis that represents the level of the sleeping state of the segments representing the predetermined period.

Preferably, the first discrimination unit discriminates the sleeping state of the subject in each unit period based on a magnitude of the body motion and/or a periodicity of the body motion in the unit period.

Preferably, the first discrimination unit includes a discrimination unit that discriminates the sleeping state of the subject in each unit period, based on a magnitude of the body motion and/or a periodicity of the body motion in the unit period, and a correction unit that corrects the sleeping state of the subject in each unit period based on a result of discriminating the sleeping state of the subject in unit periods adjacent to the unit period.

Preferably, the predetermined period is a period belonging to a prescribed time slot of one day, and the generation unit generates display data for displaying the level of the sleeping state of the subject in the time slot for a plurality of days on the same time axis.

According to another aspect of the present invention, a display method for a sleep evaluation device, for displaying a level of a sleeping state of a subject in a predetermined period on a display device with a graph along a time axis, based on a sensor signal that detects body motion of the subject output from a sensor, includes a step of receiving input of the sensor signal, a step of discriminating the sleeping state of the subject for each unit period, based on the sensor signal, a step of discriminating the level of the sleeping state of the predetermined period which consists of continuous unit periods, based on a sleeping state discrimination result for each unit period, a step of deciding a display mode for each predetermined period, according to the level of the sleeping state of the predetermined period, and a step of generating display data that represents the level of the sleeping state of the predetermined period with the display mode.

Advantageous Effects of Invention

According to this invention, the burden on the person being evaluated can be eased and levels of the sleeping state of the person being evaluated can be acquired. Furthermore, the levels of the sleeping state can be presented in an easily understandable manner.

BRIEF DESCRIPTION OF DRAWINGS

FIG. 9A is a diagram showing a specific example of discrimination results of a discrimination unit shown in FIG. 6, FIG. 9B is a diagram showing a specific example of correction of discrimination results shown in FIG. 9A, and FIG. 9C is a diagram showing a specific example of sleep level determination results for each fixed period.

FIG. 10 is a diagram showing a first specific example of the display of sleep levels.

FIG. 11 is a diagram showing a second specific example of the display of sleep levels.

DESCRIPTION OF EMBODIMENTS

Embodiments of the present invention will be described hereinafter, with reference to the drawings. In the following description, the same reference signs are given to the same components and constituent elements. The names and functions thereof are also the same.

External Appearance

Figure 1:
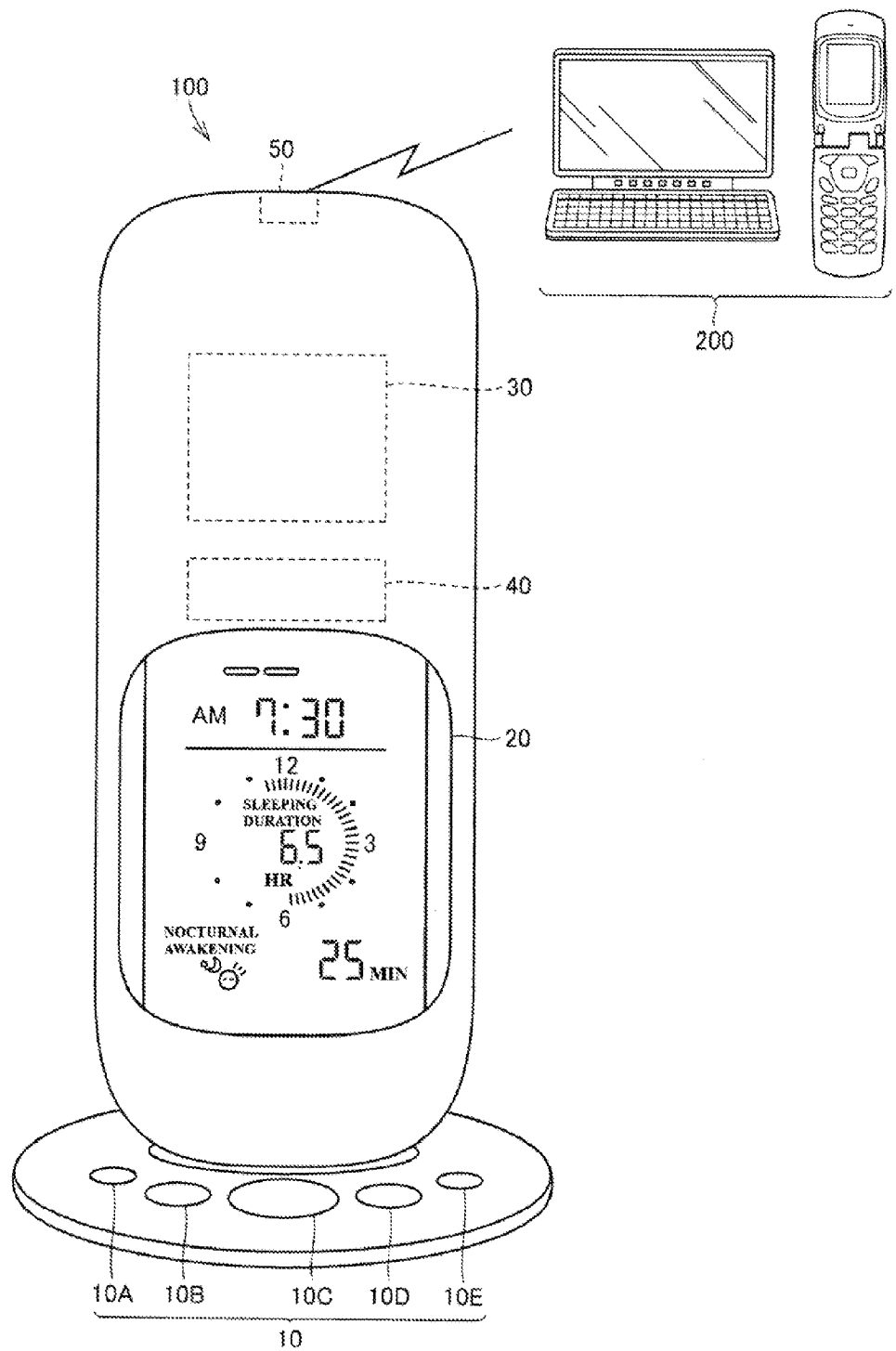
FIG. 1 is a diagram showing a specific example of the external appearance of a sleep level measurement device (hereinafter, abbreviated to "measurement device") according to an embodiment of the present invention.

FIG. 1 is a diagram showing a specific example of the external appearance of a sleep level measurement device (hereinafter, abbreviated to "measurement device") 100 according to the present embodiment. Also, FIG. 2 is a schematic view representing a lateral face of the measurement device 100, and FIG. 3 is a schematic view of the external appearance seen from diagonally above.

Figure 2:
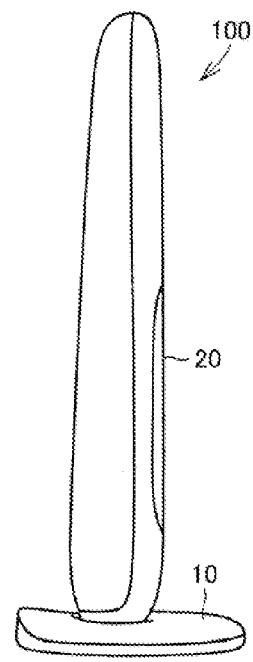
FIG. 2 is a schematic view representing a lateral face of the measurement device.
Figure 3:
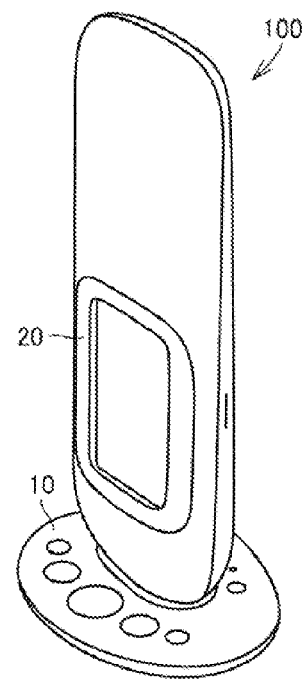
FIG. 3 is the schematic view of the external appearance of the measurement device seen from diagonally above.

Referring to FIGS. 1 to 3, a measurement device 100 has, as one example, an external appearance in which a casing that is a rectangular parallelepiped or elongated in shape with rounded corners is placed on a base.

Referring to FIG. 1, an operation button (or a group of buttons) 10 is disposed on the surface of the base, and a display unit 20 is disposed on the surface of the casing that is placed on the base. Also, a sensor 30 and a control unit 40 are incorporated into the casing.

In the subsequent description, the surface of the casing on which the display unit 20 is provided will be called the front face of the measurement device 100.

The measurement device 100 has a communication unit 50 for performing wireless or wired communication. The communication unit 50 is, as one example, provided at the opposite end of the casing to the base. The measurement device 100 is connected to a display device 200 such as a personal computer (hereinafter, PC) or a mobile phone, using the communication unit 50, and outputs display data to the display device 200.

Hardware Configuration

Figure 4:
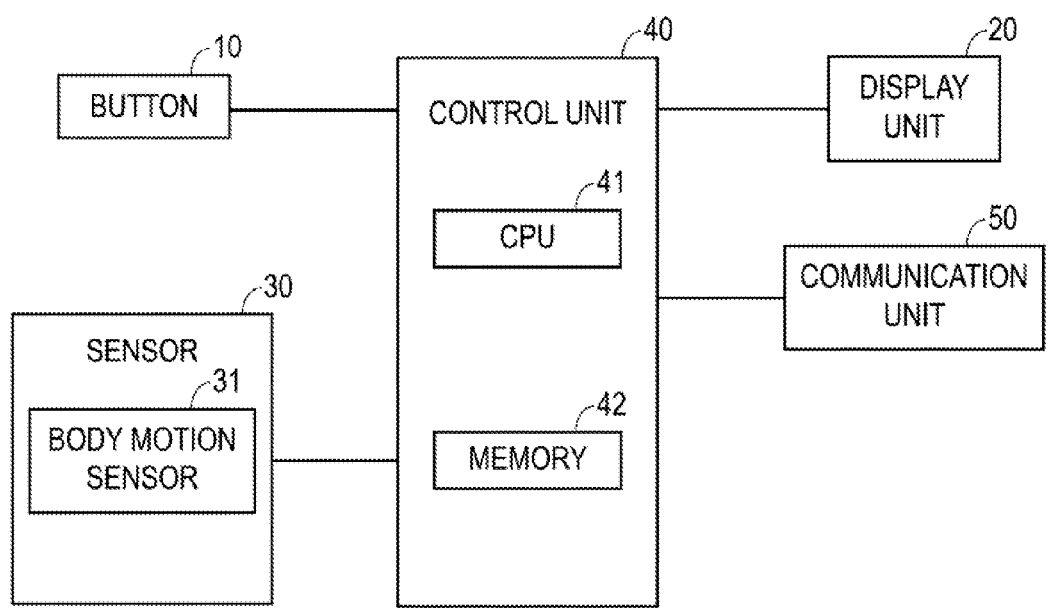
FIG. 4 is a block diagram showing a specific example of the hardware configuration of the measurement device.

FIG. 4 is a block diagram showing a specific example of the hardware configuration of the measurement device 100.

Referring to FIG. 4, the button 10, the sensor 30, the display unit 20 and the communication unit 50 are all connected to the control unit 40.

The button 10 outputs an operation signal to the control unit 40 as a result of being operated by a user.

The sensor 30 includes a body motion sensor 31 and outputs a sensor signal to the control unit 40. A Doppler sensor is preferably used as the body motion sensor 31. In the subsequent description, the body motion sensor 31 is assumed to be a Doppler sensor. Alternatively, an ultrasonic sensor or an infrared sensor may be used.

The body motion sensor 31, which is a Doppler sensor, has an output unit for outputting radio waves for use in measurement and a receiving unit that are not shown. The receiving unit receives radio waves reflected from the surface of a measurement body among radio waves output from the output unit, and outputs a sensor signal that depends on the change in frequency from the output radio waves.

Note that a camera may be provided instead of the body motion sensor 31 as the mechanism for detecting body motion, and body motion may be detected by performing image analysis in the control unit 40.

The control unit 40 includes a CPU 41 for performing overall control, and a memory 42 for storing programs that are executed by the CPU 41, and the like. The control unit 40 computes a sleep level discussed later and generates display data for displaying the sleep level, by the CPU 41 executing a program for performing display stored in the memory 42, and executing an operation using an input operation signal and sensor signal.

The control unit 40 executes display control for performing screen display on the display unit 20 based on the display data. Furthermore, communication control for transmitting display data from the communication unit 50 to the display device 200 is executed.

The communication unit 50 may communicate directly with the display device 200, by wireless communication such as infrared communication or communication utilizing Bluetooth (registered trademark), for example, or may have an Internet connection function and communicate with the display device 200 via the Internet.

Furthermore, the communication unit 50 may have a wireless LAN (Local Area Network) server function, and transmit display data discussed below that is expressed in a markup language such as HTML (Hypertext Markup Language), for example, to the display device 200 accessed by a wireless LAN connection.

Exemplary Usage

Figure 5:
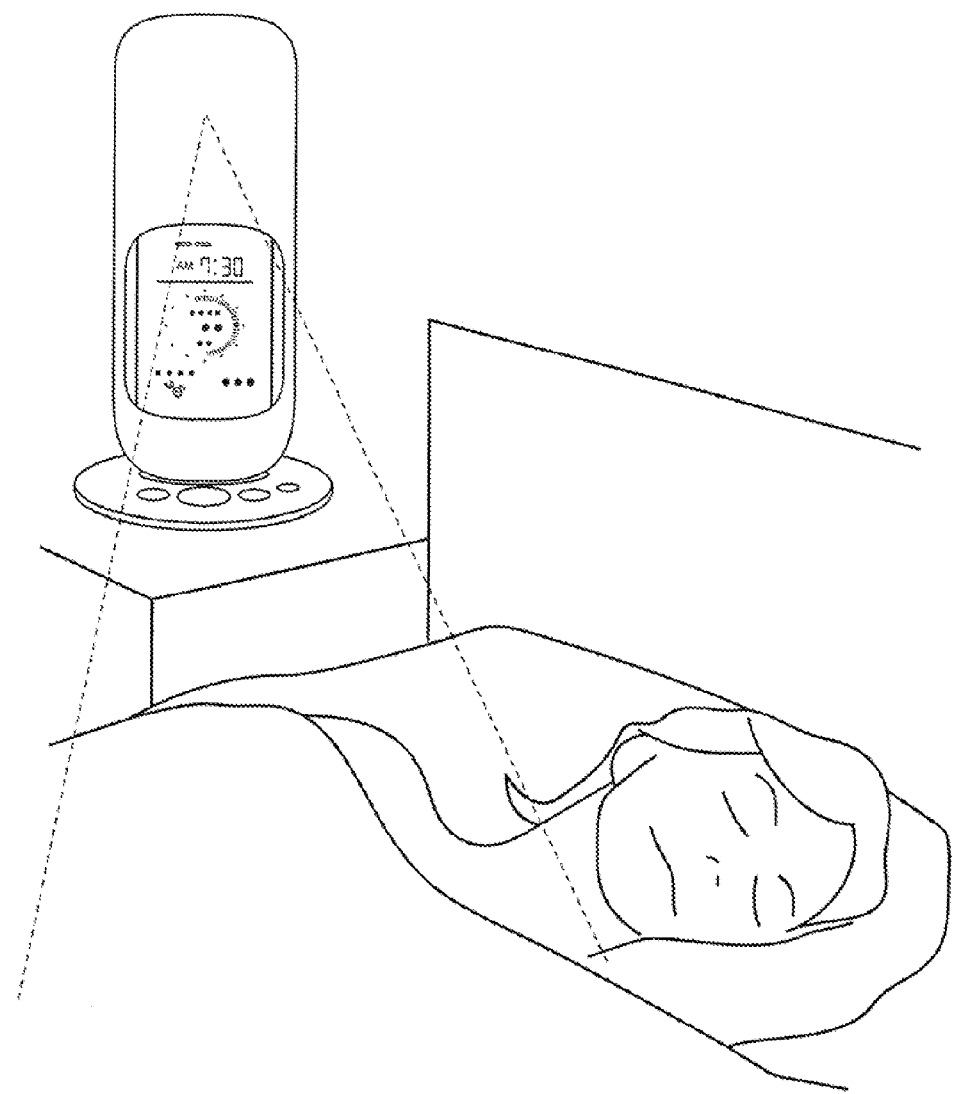
FIG. 5 is a diagram illustrating an exemplary usage of the measurement device.

FIG. 5 is a diagram illustrating an exemplary usage of the measurement device 100.

Referring to FIG. 5, the measurement device 100 is installed in proximity to the person being evaluated who is asleep (e.g., bedside) as an example. To perform the measurement operation in this state, radio waves are output from the body motion sensor 31 which is a Doppler sensor.

The radio waves output from the body motion sensor 31 reach mainly the vicinity of the chest and shoulders of the person who is sleeping, and the change in frequency of the waves reflected therefrom is output to the control unit 40 as a sensor signal. The control unit 40 detects body motion, such as chest movement of the person who is sleeping or the person rolling over in his or her sleep, based on the change in frequency, and determines the sleep level based on that detection results.

Functional Configuration

Figure 6:
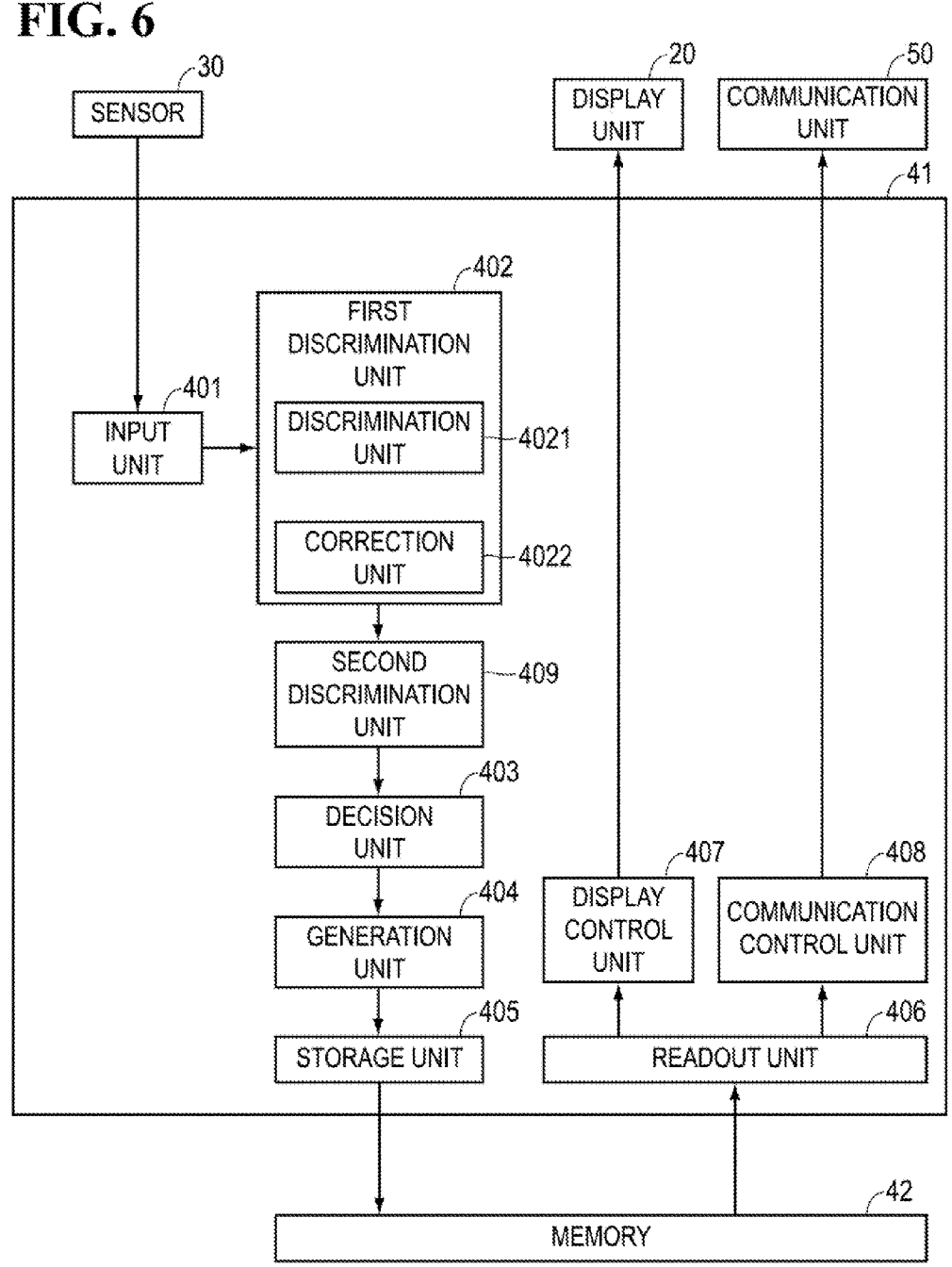
FIG. 6 is a block diagram showing a specific example of the functional configuration for determining sleep level in the measurement device.

FIG. 6 is a block diagram showing a specific example of the functional configuration for determining the sleep level in the measurement device 100. The functions represented in FIG. 6 are mainly formed on the CPU 41 by the CPU 41 executing programs stored in the memory 42, but at least some of the functions may be formed by a hardware configuration such as electrical circuitry.

Referring to FIG. 6, the measurement device 100 includes an input unit 401 for receiving input of the sensor signal output from the sensor 30, a first discrimination unit 402 for discriminating the sleeping state of a unit period based on the sensor signal, a second discrimination unit 409 for discriminating a level of the sleeping state in a fixed period consisting of a predetermined number of continuous unit periods, based on a discrimination result for each unit period, a decision unit 403 for deciding a display mode of the fixed period based on the level of the sleeping state, a generation unit 404 for generating display data for displaying the sleep level based on the decided display mode, a storage unit 405 for executing processing for storing display data in the memory 42, a readout unit 406 for reading out display data from the memory 42, a display control unit 407 for executing processing for displaying read display data on the display unit 20, and a communication control unit 408 for executing processing for transmitting display data to the display device 200 using the communication unit 50.

In the example of FIG. 6, the input unit 401 receives the sensor signal output directly from the sensor 30, but a configuration may be adopted in which the sensor signal is temporarily stored to a predetermined area of the memory 42, and is read out from there by the input unit 401 when performing a display operation.

Sleep Level Discrimination Method

Here, the sleep level discrimination method of the second discrimination unit 409 will be described.

Figure 7:
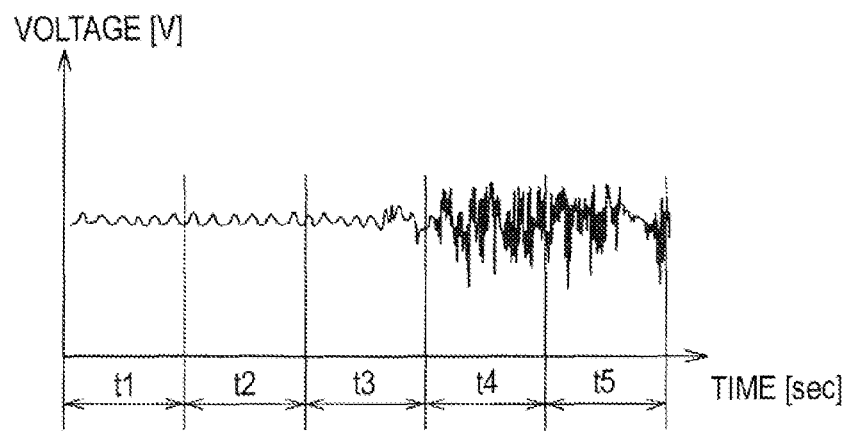
FIG. 7 is a diagram showing a specific example of a sensor signal output from a body motion sensor that is a Doppler sensor.

FIG. 7 is a diagram showing a specific example of the sensor signal output from the body motion sensor 31 which is a Doppler sensor. FIG. 7 represents the temporal change in voltage that is related to the phase displacement between the carrier wave from the body motion sensor and the reflected wave from the surface of the person being evaluated.

Referring to FIG. 7, the waveform represented by the sensor signal is a composite wave that includes a waveform representing the body motion (chest movement) of the person being evaluated that is associated with breathing (hereinafter also called a respiratory waveform) and a waveform representing body motion other than breathing such as the person rolling over in his or her sleep or the like (hereinafter also called a body motion waveform).

Figure 8A:
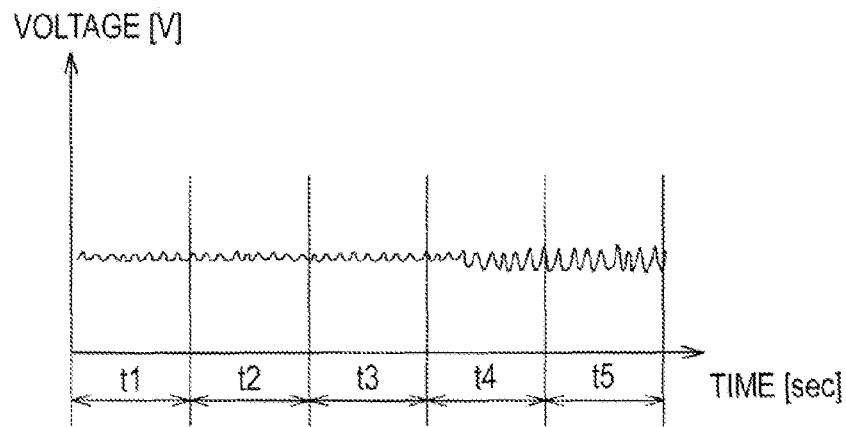
FIG. 8A is a diagram showing a specific example of a respiratory waveform separated from the waveform represented in FIG. 7.
Figure 8B:
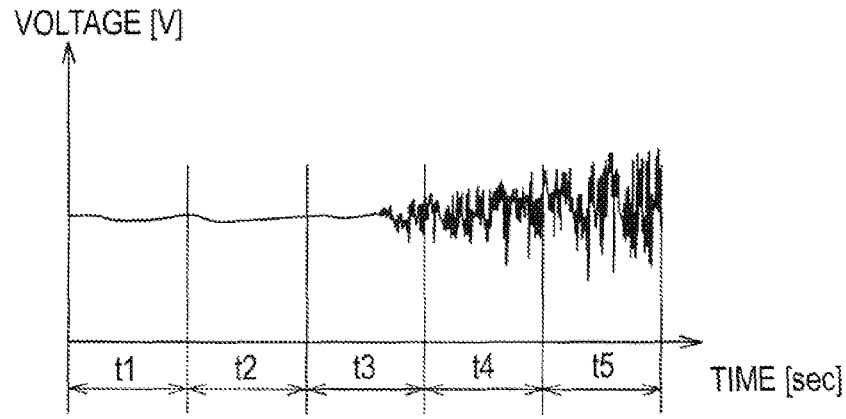
FIG. 8B is a diagram showing a specific example of a body motion waveform separated from the waveform represented in FIG. 7.

FIGS. 8A and 8B are diagrams showing specific examples of a respiratory waveform and a body motion waveform separated from the waveform represented in FIG. 7.

The respiratory waveform of a person who is in a stable sleep state has periodicity. Accordingly, in the case where the periodicity of the respiratory waveform is within a predetermined range, that is, when variation in the cycle of the respiratory waveform is within a predetermined range, the person can generally be said to be in a stable sleep state.

Also, when a person is in a stable sleep state, there is unlikely to be any body motion other than breathing such as rolling over in his or her sleep. Accordingly, a person can generally be said to be in a stable sleep state when the amplitude of the body motion waveform is within a predetermined range, and can be said to not be in a stable sleep state in the case where the amplitude is not within the predetermined range, since there is body motion.

Accordingly, it can be discriminated whether or not the person being evaluated is in a stable sleep state with regard to a given period, based on the periodicity of the respiratory waveform or the magnitude of body motion other than breathing in that period. Note that although the sleeping state is discriminated using both the respiratory waveform and the body motion waveform in this example, it is possible to use only one of the waveforms.

As shown in FIG. 6, the first discrimination unit 402 includes a discrimination unit 4021 and a correction unit 4022.

The discrimination unit 4021 separates the waveform that is based on the input sensor signal shown in FIG. 7 into the respiratory waveform and the body motion waveform shown in FIGS. 8A and 8B. The discrimination unit 4021 then discriminates whether the person being evaluated is in a stable sleep state, every prescribed unit period (periods t1, t2, t3, t4, t5 in FIG. 7), based on the respective waveforms. The unit period here is around 30 seconds to 1 minute, for example. That is, if the variation in the cycle in unit period t1 of the respiratory waveform is less than a preset threshold, it is judged that periodicity is evident in the respiratory waveform in unit period t1. Also, it is judged whether the amplitude in unit period t1 of the body motion waveform is greater than or less than a preset threshold.

The discrimination unit 4021 then discriminates that the sleeping state of the person being evaluated in unit period t1 is a sleeping state (S), in the case where the respiratory waveform has periodicity in unit period t1, and the amplitude of the body motion waveform is less than the threshold. On the other hand, the discrimination unit 4021 discriminates that the sleeping state of the person being evaluated in unit period t1 is a waking state (W), in the case where the respiratory waveform does not have periodicity in unit period t1, and the amplitude of the body motion waveform is greater than the threshold. Note that the discrimination unit 4021 may be configured to discriminate that the person being evaluated is in a waking state if only one of these conditions is satisfied, or in other words, if only the respiratory waveform has periodicity in unit period t1 or the amplitude of the body motion waveform is less than the threshold.

FIG. 9A is a diagram showing a specific example of discrimination results of the discrimination unit 4021. As shown in FIG. 9A, the discrimination unit 4021 discriminates whether the person being evaluated is in a stable sleeping state or a waking state, every unit period of the waveform that is based on the input sensor signal.

However, there may also be unit periods where body motion occurs in a sleeping state or where there is no body motion and breathing is regular in a waking state. Also, there may be cases where a reflected wave from a moving object other than the person being evaluated is received, resulting in noise occurring in the body motion waveform. In view of this, preferably the correction unit 4022 corrects the discrimination result of such unit periods, according to the discrimination results of adjacent unit periods.

As one example, FIG. 9B shows a specific example of correction of discrimination results shown in FIG. 9A. Referring to FIG. 9A and FIG. 9B, in the case where the number of continuous unit periods having the same discrimination result is less than or equal to a predetermined number, and the number of unit periods continuous therebefore and thereafter having the opposite discrimination result is greater than or equal to a predetermined number, the correction unit 4022 corrects the discrimination result of those continuous unit periods having the same discrimination result to the opposite discrimination result.

Specifically, although the discrimination unit 4021 discriminates that unit period t7 in FIG. 9A is the waking state (W), there are no unit periods discriminated to be the waking state (W) that are continuous with unit period t7 (i.e., number of continuous unit periods is 1), and there is a certain number of unit periods continuous before and after unit period t7 that are discriminated to be the sleeping state (S). The unit period t13 is also in a similar state where the discrimination result is opposite.

If it is assumed that the threshold (first threshold) for the continuous number of discrimination results of the targeted unit period is 2, and the threshold (second threshold) for the continuous number of discrimination results of unit periods before and after the targeted unit period is 2, these conditions are satisfied for unit period t7 in that the one continuous unit period discriminated to be the waking state (W) is less than the first threshold, and the three continuous unit periods before and after unit period t7 that have the opposite discrimination result are greater in number than the second threshold. Accordingly, the correction unit 4022 corrects the discrimination result of unit period t7 to the sleeping state (S) which is the opposite discrimination result.

Similarly, the correction unit 4022 also corrects the discrimination result of unit period t13 to the waking state (W) which is the opposite discrimination result.

Next, the second discrimination unit 409 discriminates the sleep level for a fixed period consisting of continuous unit periods, based on the discrimination result of each unit period. The unit period here is around 5 minutes to 10 minutes, for example.

Here, the sleep levels denote levels of the sleeping state defined in terms of the regularity of breathing and the existence and continuity of body motion. Specific examples include:

Level 1: Sleeping state with no body motion and regular breathing;
Level 2: Sleeping state with one-off body motion;
Level 3: Sleeping state with continuous body motion;
Level 4: Waking state with continuous body motion that is ongoing; and
Level 5: Full waking state.

Figure 13:
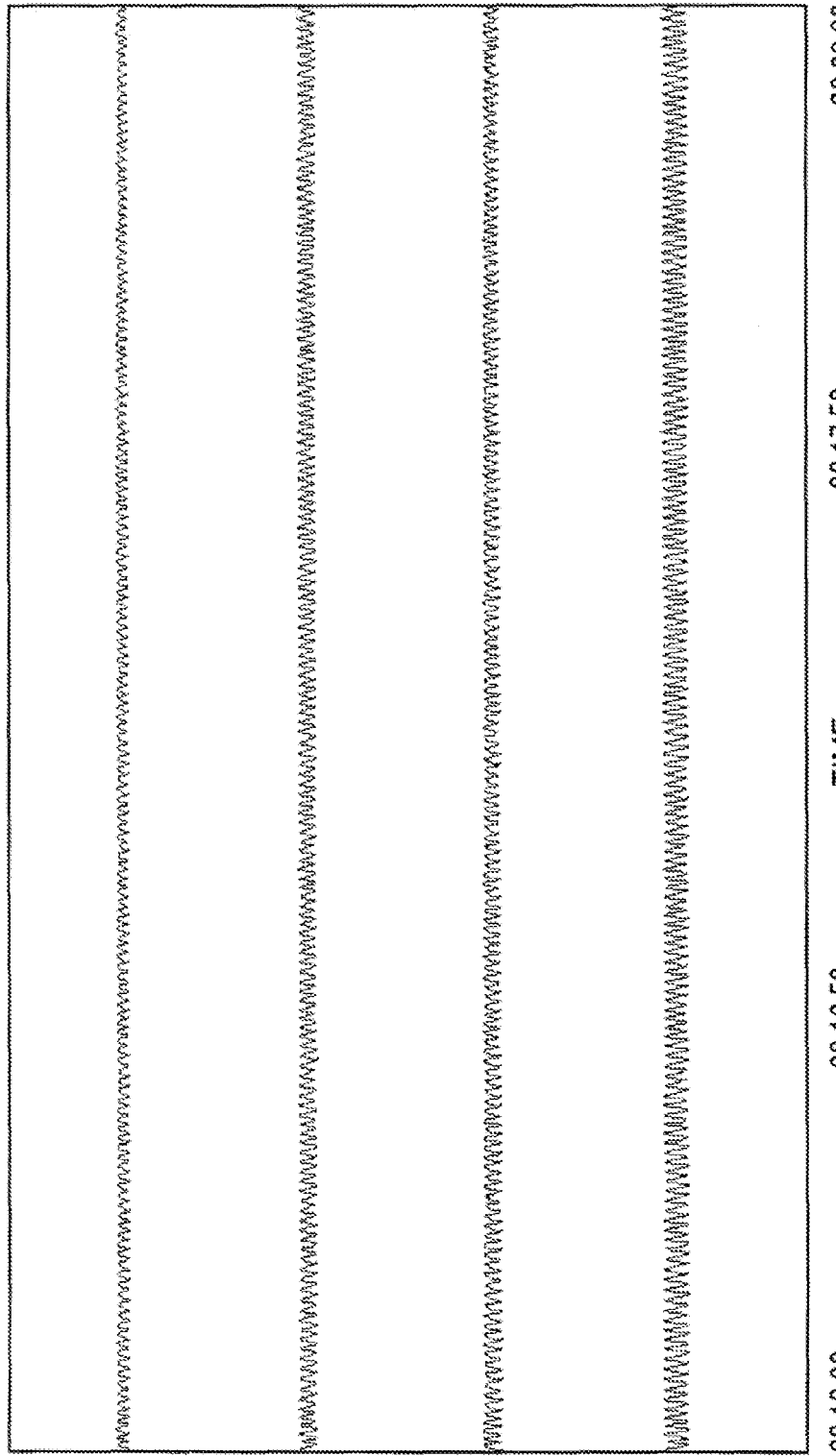
FIG. 13 is a diagram showing specific examples of typical waveforms of a sensor signal that correspond to a sleep level.
Figure 14:
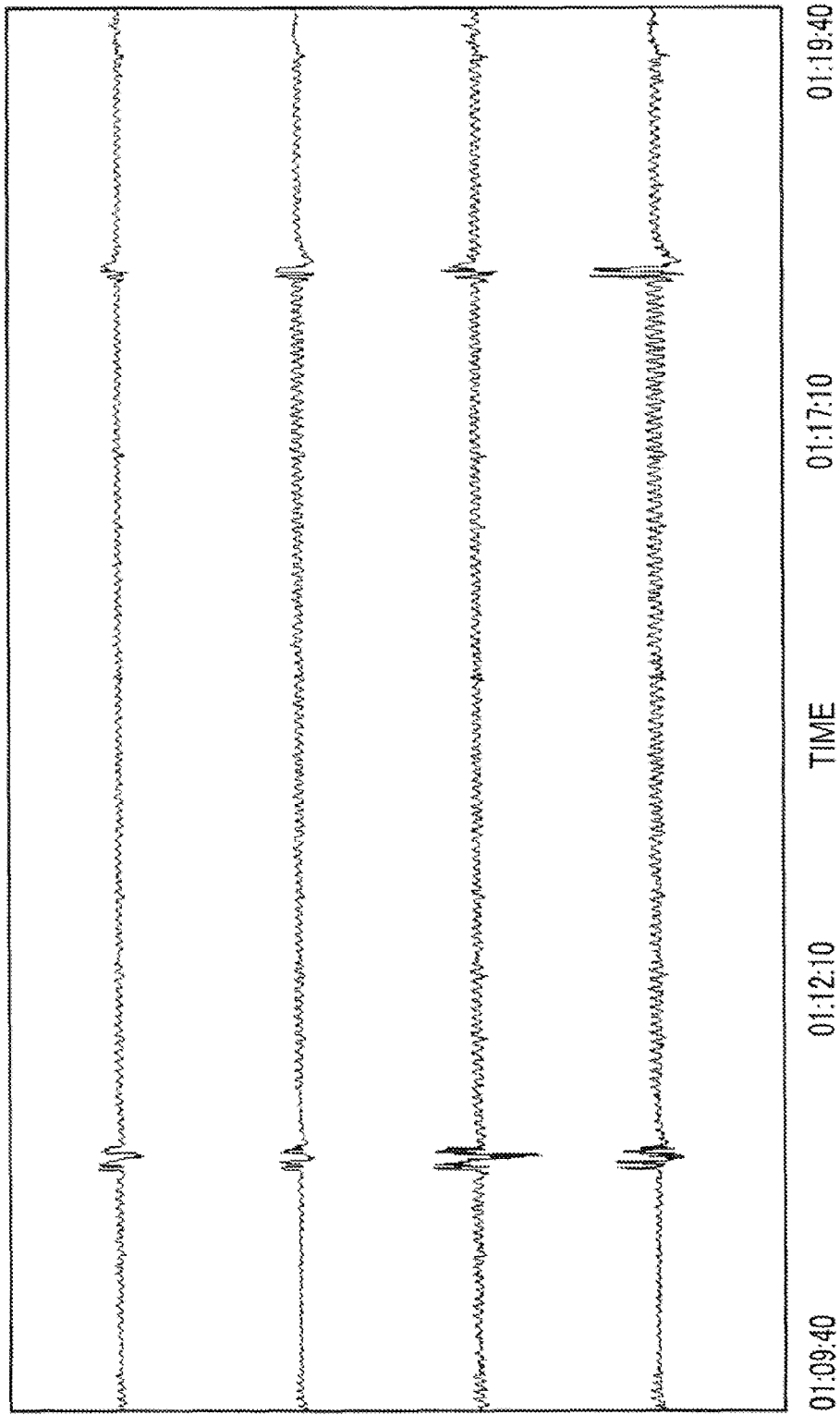
FIG. 14 is a diagram showing specific examples of typical waveforms of a sensor signal that correspond to a sleep level.
Figure 15:
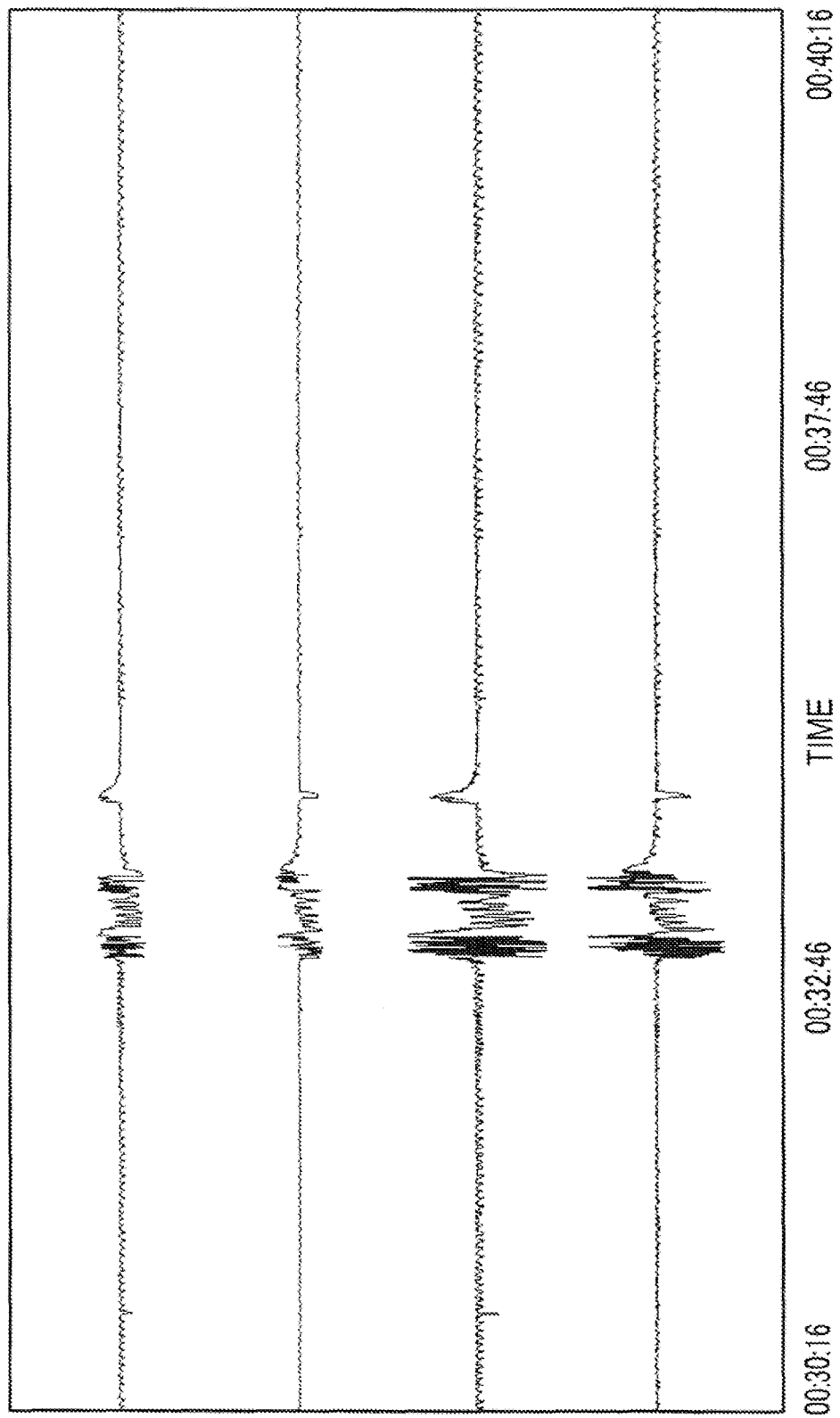
FIG. 15 is a diagram showing specific examples of typical waveforms of a sensor signal that correspond to a sleep level.
Figure 16:
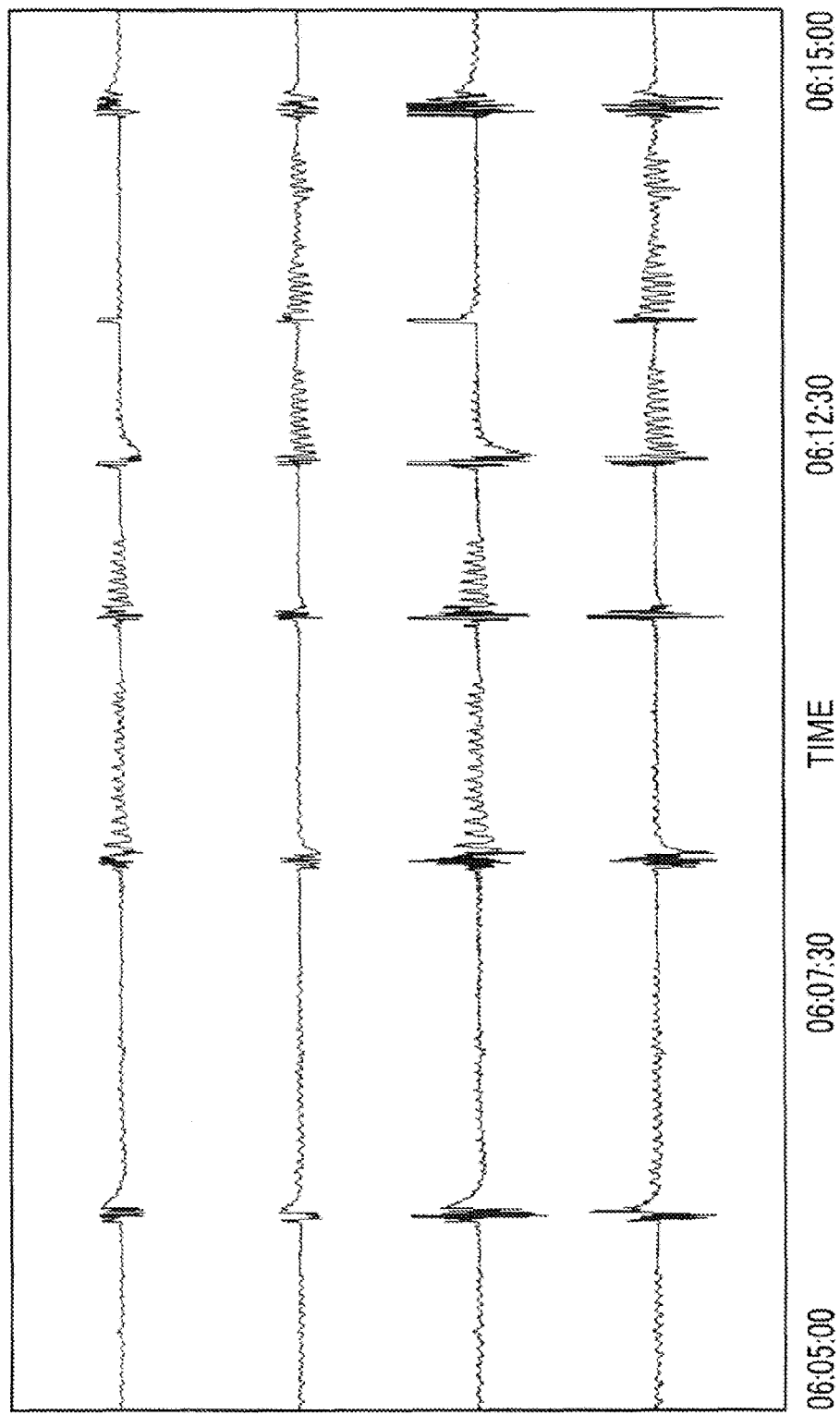
FIG. 16 is a diagram showing specific examples of typical waveforms of a sensor signal that correspond to a sleep level.
Figure 17:
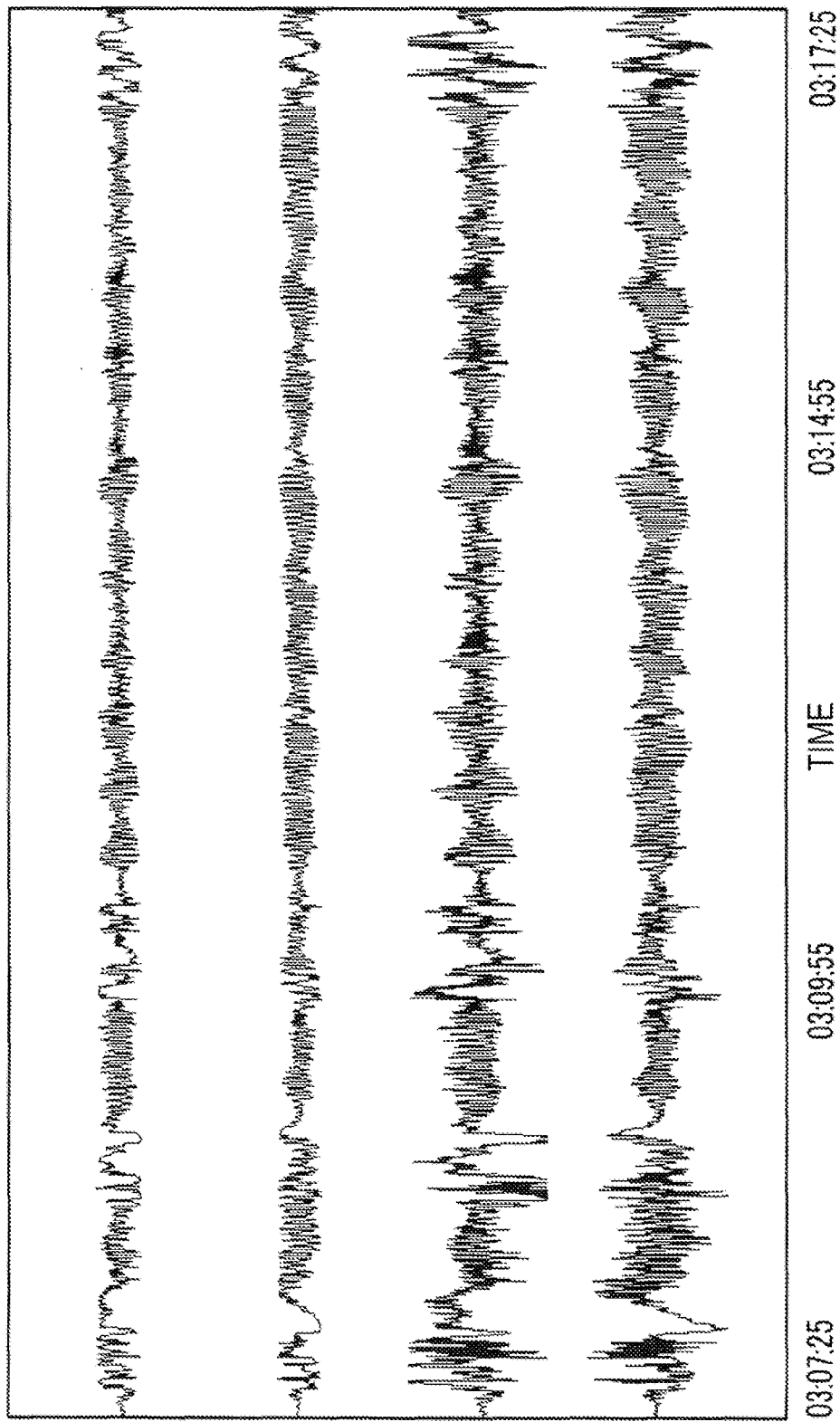
FIG. 17 is a diagram showing specific examples of typical waveforms of a sensor signal that correspond to a sleep level.
Figure 18:
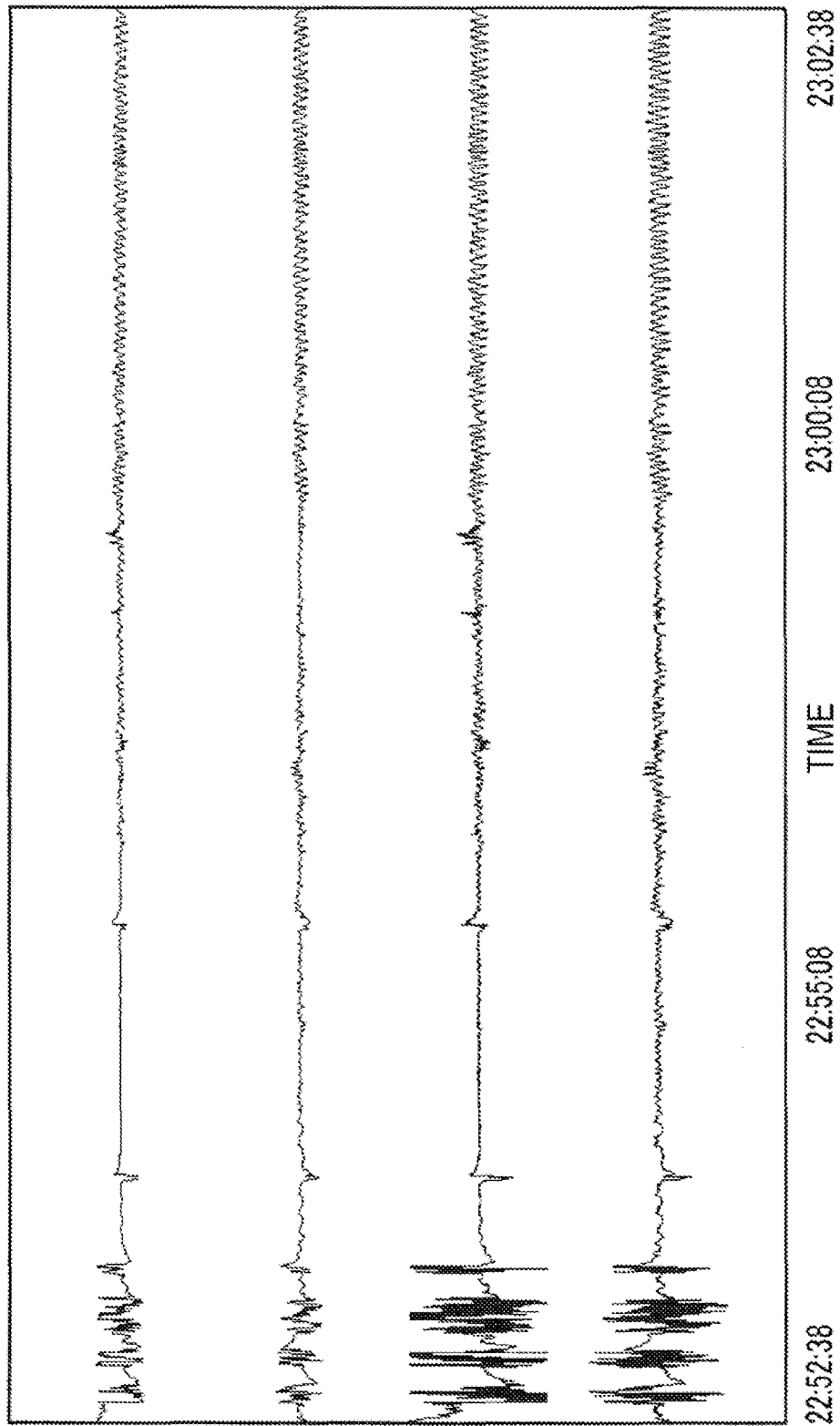
FIG. 18 is a diagram showing specific examples of typical waveforms of a sensor signal that correspond to a sleep level.
Figure 19:
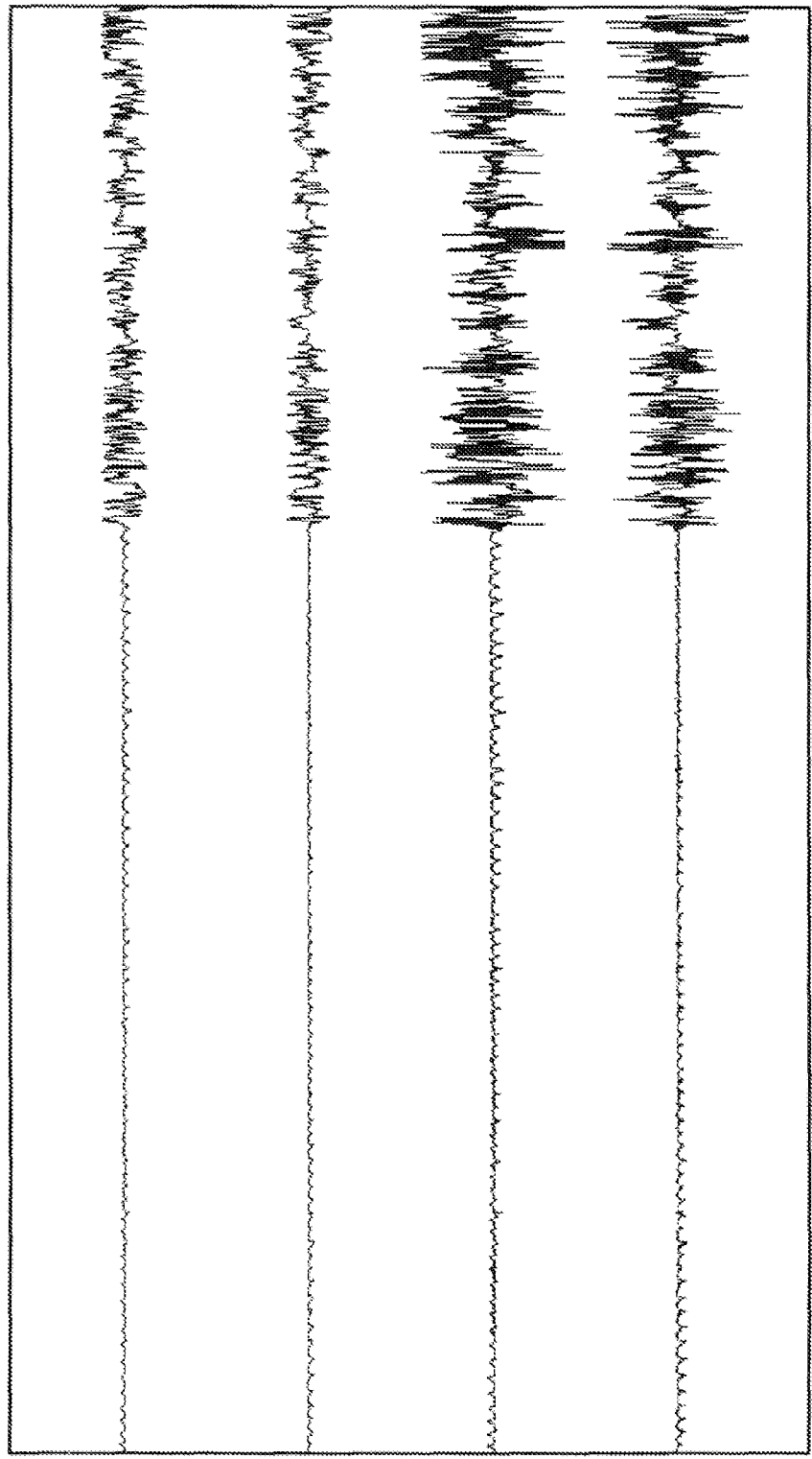
FIG. 19 is a diagram showing specific examples of typical waveforms of a sensor signal that correspond to a sleep level.

The second discrimination unit 409 stores, as a determination value for each level, a continuous number and a ratio of discrimination results of the unit periods constituting a fixed period. As an example, FIG. 13 represents specific examples of typical waveforms of the sensor signal in the case of the above level 1, FIG. 14 represents specific examples of typical waveforms of the sensor signal in the case of the above level 2, FIG. 15 and FIG. 16 represent specific examples of typical waveforms of the sensor signal in the case of the above level 3, FIG. 17 represents specific examples of typical waveforms of the sensor signal in the case of the above level 4, FIG. 18 represents typical waveforms of the sensor signal in the case of the above level 5, particularly waveforms of the sensor signal when the person being evaluated is going to sleep, and FIG. 19 represents typical waveforms of the sensor signal in the case of the above level 5, particularly waveforms of the sensor signal when the person being evaluated is waking up. The second discrimination unit 409 prestores, as a determination value for each level, a continuous number and a ratio of discrimination results represented in the waveforms of these sensor signals. FIG. 9C is a diagram representing a specific example of the sleep level determination result for each fixed period. That is, referring to FIG. 9B and FIG. 9C, the second discrimination unit 409 discriminates the sleep level for each fixed period, by comparing the continuous number of the determination result with the stored determination value, and comparing the ratio of the determination results with the determination value, for the continuous unit periods constituting the fixed period.

Display Examples

With regard to a given time slot, the measurement device 100 sets, every fixed period belonging to that time slot, segments representing the fixed period to a display mode that depends on the sleep level, and displays the segments in chronological order.

FIG. 10 is a diagram showing a first specific example of the display of sleep levels.

Referring to FIG. 10, as the first example, an example is shown in which segments representing each fixed period are arranged in chronological order, and the respective segments are displayed with colors that depend on the sleep level of the fixed period. Note that, in FIG. 10, the display colors that depend on sleep level are expressed using different types of hatching, for convenience of display. The same applies to a second display example discussed later.

In order to perform display according to the first example, the decision unit 403 prestores display colors that depend on sleep level, and decides the display color according to the discriminated sleep level, every fixed period. The generation unit 404 then generates display data for setting the segments corresponding to that fixed period to the decided display color.

As a result of display processing based on this display data being performed by the display control unit 407 or being performed by the display device 200 to which the display data has been transmitted by the communication unit 50 under the control of the communication control unit 408, display as shown in FIG. 10 is realized on a display unit thereof.

In FIG. 10, every fixed period belonging to time slots of one day, for example, the sleep level of the person being evaluated for that fixed period is displayed with a corresponding color. Thus, the user is able to grasp at a glance the transition in the sleep level of the person being evaluated for each fixed period in any given time slot.

Furthermore, in order to display a display screen such as shown in FIG. 10, preferably the generation unit 404 generates display data that represents the segments representing each fixed period, over two or more consecutive days arranged by day on the same time axis. The user is thereby able to easily compare the transition in the sleep level of the person being evaluated for each fixed period in any given time slot over consecutive days. The same applies to the second display example discussed later.

Note that although an example is represented in FIG. 10 in which measurement results for consecutive days such as one week, for example, are displayed adjoining one another, display is not limited to consecutive days, and a configuration may be adopted in which the measurement results for a specific day such as Monday, for example, are displayed adjoining one another. The same applies to the second display example discussed later.

FIG. 11 is a diagram showing a second specific example of the display of sleep levels.

Referring to FIG. 11, as the second example, an example is shown in which segments representing each fixed period are arranged in chronological order, and, furthermore, an axis representing the sleep levels is set in a direction orthogonal to the time axis, and the respective segments are displayed at least in positions that depend on the sleep level. More preferably, as shown in FIG. 11, each segment is, furthermore, also represented with a color that depends on the sleep level of the fixed period.

In order to perform display according to the second example, the display position of the segments on the axis representing sleep level is decided. The generation unit 404 then generates display data for setting the segments corresponding to that fixed period to the decided display positions. In the case of deciding the display color together with the display position, the display color is decided similarly to the first example.

As a result of display processing based on this display data being performed by the display control unit 407 or being performed by the display device 200 to which the display data has been transmitted by the communication unit 50 under the control of the communication control unit 408, display such as shown in FIG. 11 is realized on a display unit thereof.

In FIG. 11, every fixed period belonging to time slots of one day, for example, the segments representing that fixed period are displayed, relative to the axis indicating sleep level that is orthogonal to the time axis, in positions that depend on the sleep level of the person being evaluated. Thus, the user is able to intuitively grasp at a glance the transition in the sleep levels of the person being evaluated for each fixed period in any given time slot.

Note that in the examples in FIG. 10 and FIG. 11, display that is expressed with segments every fixed period and in which the segments are arranged in chronological order is performed. However, the present invention is not limited to display using segments, and other forms of display may be performed, such as display in which an entire time slot specified in advance is converted to a bar graph and corresponding times are set to display colors that depend on sleep level.

Operation Flow

Figure 12:
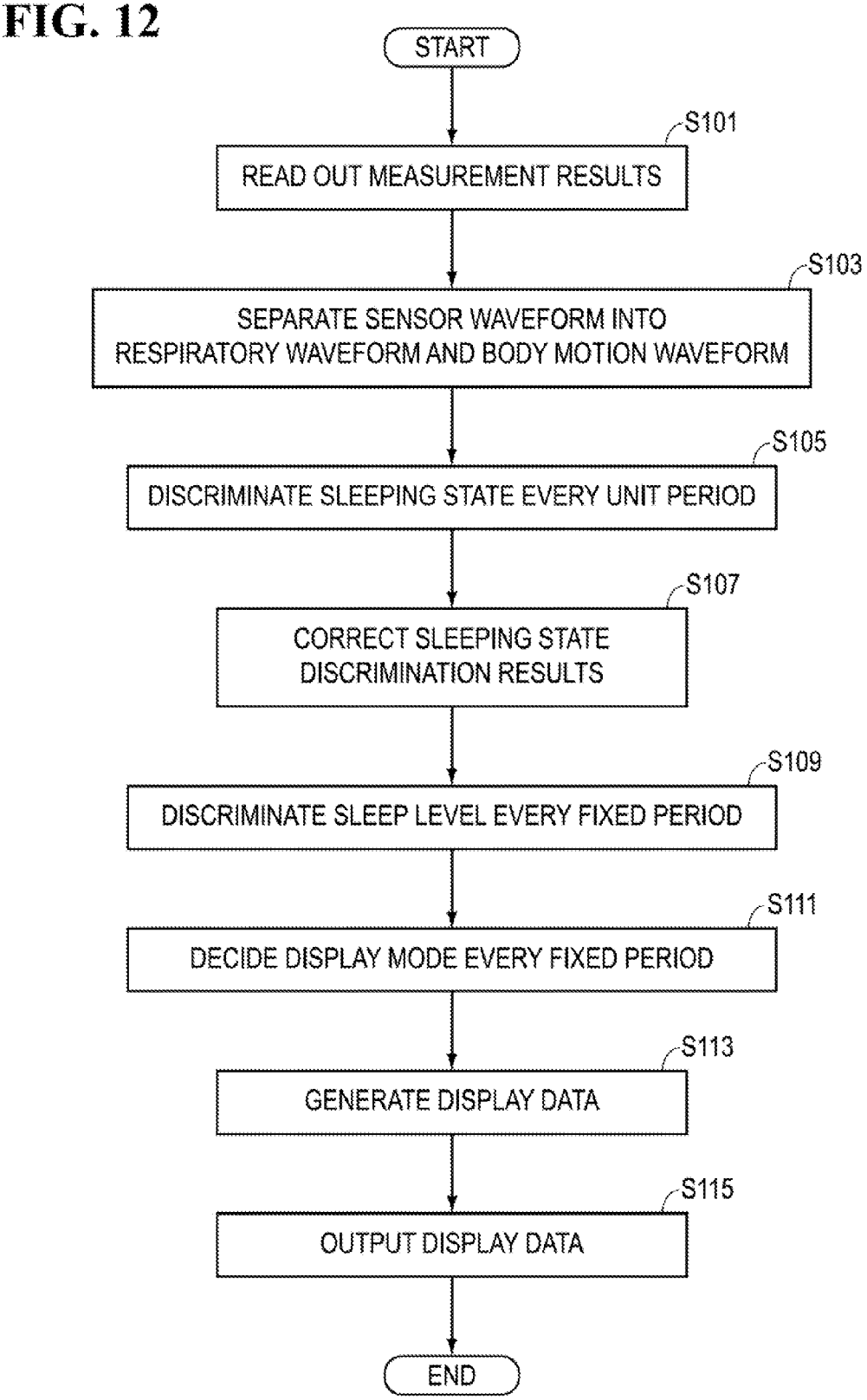
FIG. 12 is a flowchart showing a specific example of an operation flow for display by the measurement device.

FIG. 12 is a flowchart showing a specific example of the operation flow for performing display in the measurement device 100. The operation shown in the flowchart of FIG. 12 may, for example, be started by receiving the pressing of a display button (not shown) included as a button 10, or may be automatically started at a predetermined timing (e.g., at a prescribed time). This operation is realized by the CPU 41 reading out and executing a display program stored in the memory 42 to exhibit the functions shown in FIG. 6.

Referring to FIG. 12, when the operation for performing display has been started, the CPU 41, at step S101, reads out the sensor signal stored in a predetermined storage area of the memory 42, and, at step S103, separates the waveform represented by the sensor signal into a respiratory waveform and a body motion waveform. For example, the waveform of the sensor signal read out at step S101 is, in the case of being the waveform in FIG. 7, separated, at step S103, into the respiratory waveform shown in FIG. 8A and the body motion waveform shown in FIG. 8B, for example.

At step S105, the CPU 41 discriminates, for each preset unit period, the sleeping state in that period, respectively for the obtained respiratory waveform and body motion waveform, based on the periodicity of the respiratory waveform and/or the magnitude of the amplitude of the body motion waveform for each unit period. Furthermore, at step S107, the CPU 41 corrects the discrimination results of step S105, according to the discrimination results of adjacent unit periods. Furthermore, at step S109, the CPU 41 discriminates the sleep level for each fixed period consisting of continuous unit periods, based on the discrimination result of each unit period.

At step S11, the CPU 41 then decides the display mode for each fixed period, based on the discrimination results of step S109. For example, in the case of performing display according to the first example shown in FIG. 10, the CPU 41, at step S111, decides the display color for each fixed period based on the sleep level discrimination results. Alternatively, in the case of performing display according to the second example shown in FIG. 11, the CPU 41, at step S111, decides the display position (height on axis representing sleep level) of the segments representing each fixed period, based on the sleep level discrimination results, together with deciding the display color of the fixed period.

At step S113, the CPU 41 generates, for a time slot that is specified in advance for display, display data in which segments representing each fixed period belonging to that time slot are arranged along the time axis, and outputs the display data at step S115. In the case of performing display with the display unit 20 provided in the measurement device 100, the display data is output to the display unit 20. In the case of performing display on the display device 200, the display data is output to the display device 200 from the communication unit 50.

Effects of Embodiment Examples

Performing the above operation in the measurement device 100 enables the sleep levels of the person being evaluated to be measured in a non-invasive manner. Furthermore, measurement results are displayed as shown in FIG. 10 and FIG. 11, for example. That is, the sleep levels are presented using display modes such as color and display position.

Figure 20:
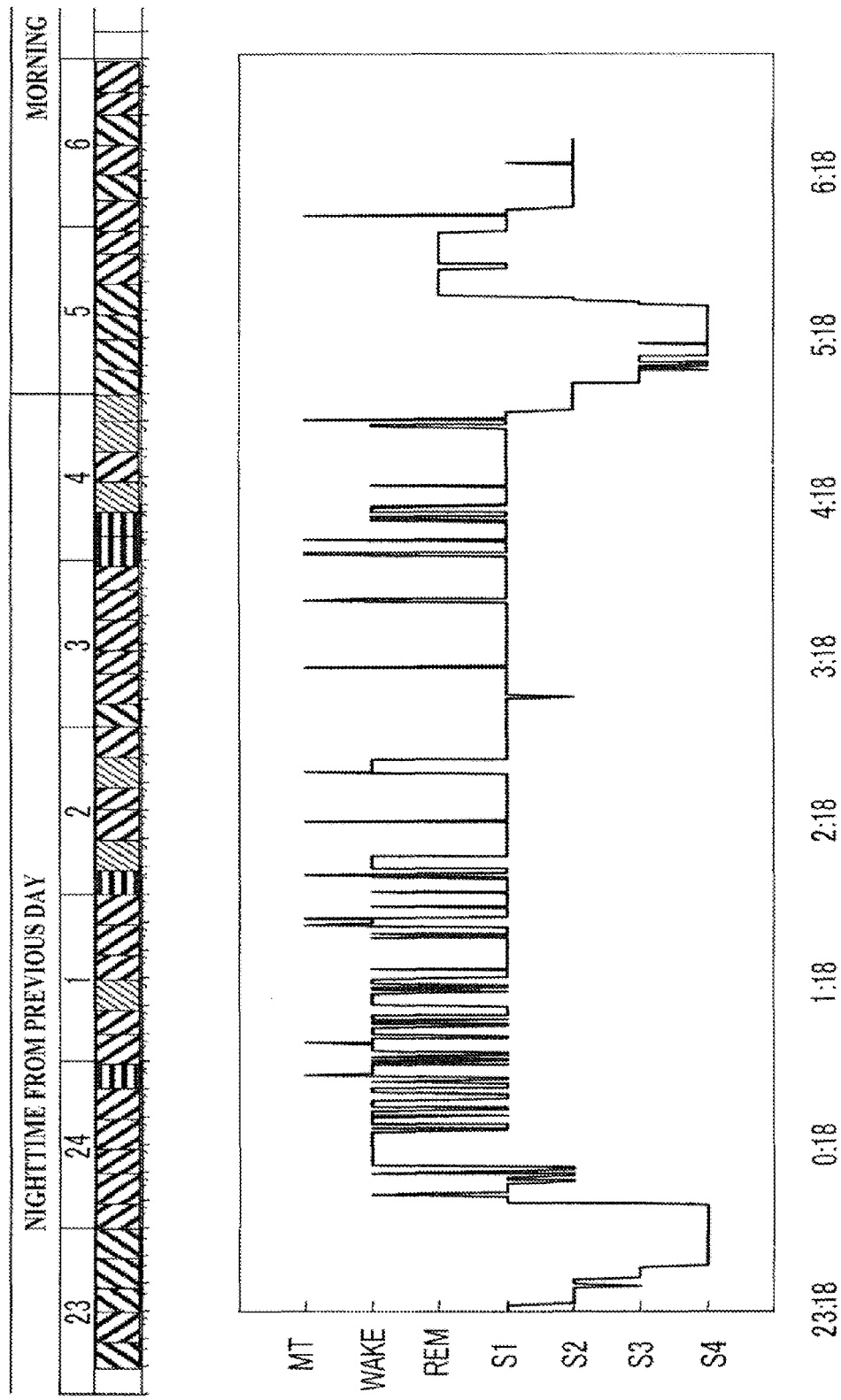
FIG. 20 is a diagram in which results obtained by the inventors performing measurement using the measurement device on a subject are represented alongside a somnogram of polysomnography (PSG) performed on the subject.

The burden on the person being evaluated can thereby be eased and his or her sleep levels can be grasped at a glance. FIG. 20 is a diagram in which actual results obtained by the inventors performing measurement using the measurement device 100 on a subject are represented alongside a somnogram of polysomnography (PSG) performed on the subject.

As shown in FIG. 20, it is clear that, in the case where the measurement device 100 is used, sleep levels that are correlated with the depth of sleep represented by the polysomnography (PSG) results are obtained. Thus, using the measurement device 100 enables the burden on the person being evaluated to be eased and sleep levels that can be generally interpreted similarly to depth of sleep to be obtained in a non-invasive manner.

Furthermore, as shown in FIG. 10 and FIG. 11, by displaying the measurement results for a plurality of measurement periods with the time axes aligned, the sleep levels of the person being evaluated can be compared for those measurement periods, and his or her sleep patterns can be easily checked.

Although embodiments of the present invention have been described above, the embodiments disclosed herein are to be considered in all respects as illustrative and not restrictive. The scope of the invention is defined by the claims, and all changes that come within the meaning and range of equivalency of the claims are intended to be embraced therein.

REFERENCE SIGNS LIST 10 button
20 display unit
30 sensor
31 body motion sensor
40 control unit
41 CPU
42 memory
50 communication unit
100 measurement device
200 display device
401 input unit
402 first discrimination unit
403 decision unit
404 generation unit
405 storage unit
406 readout unit
407 display control unit
408 communication control unit
409 second discrimination unit
4021 discrimination unit
4022 correction unit

The invention claimed is:

1. A sleep evaluation device comprising:
a body motion detection device that detects body motion of a subject; and
an arithmetic operation device that generates display data that displays a level of a sleeping state of the subject, out of a plurality of levels of the sleeping state of the subject, in a predetermined period having a plurality of unit periods on a display device with a graph along a time axis, based on a detection result of the body motion detection device, the arithmetic operation device including:
a first discrimination device that discriminates the sleeping state of the subject for each unit period, based on the detection result of the body motion detection device;
a second discrimination device that discriminates the level of the sleeping state of the predetermined period which consists of a predetermined number of continuous unit periods, based on the sleeping state for each unit period discriminated by the first discrimination device providing a continuous number of discrimination results where the sleeping state is found and a ratio of a number of unit periods with the discrimination results where the sleeping state is found to a total number of the unit periods within the predetermined period, and based on a stored determination value for each of the plurality of levels of the sleeping state;
a decision device that decides a display mode for each predetermined period, according to the level of the sleeping state of the predetermined period; and
a generation device that generates display data that represents the level of the sleeping state of the predetermined period with the display mode.

2. The sleep evaluation device according to claim 1, wherein the display data is data that displays segments representing the predetermined period continuously along the time axis, and
the decision device decides the display mode of the segments representing the predetermined period, according to the level of the sleeping state of the predetermined period.

3. The sleep evaluation device according to claim 2, wherein the decision device decides a color that depends on the level of the sleeping state, as a color of the segments representing the predetermined period.

4. The sleep evaluation device according to claim 2, wherein the display data is data that displays the segments representing the predetermined period continuously along the time axis, with respect to an axis representing the level of the sleeping state that is orthogonal to the time axis, and
the decision device decides a position that depends on the level of the sleeping state, as a display position in a direction of the axis that represents the level of the sleeping state of the segments representing the predetermined period.

5. The sleep evaluation device according to claim 1, wherein the first discrimination device discriminates the sleeping state of the subject in each unit period based on a magnitude of the body motion and/or a periodicity of the body motion in the unit period.

6. The sleep evaluation device according to claim 1, wherein the first discrimination device includes:
a discrimination device that discriminates the sleeping state of the subject in each unit period, based on a magnitude of the body motion and/or a periodicity of the body motion in the unit period; and
a correction device that corrects the sleeping state of the subject in each unit period based on a result of discriminating the sleeping state of the subject in unit periods adjacent to the unit period.

7. The sleep evaluation device according to claim 1, wherein the predetermined period is a period belonging to a prescribed time slot of one day, and
the generation device generates display data that displays the level of the sleeping state of the subject in the time slot for a plurality of days on the same time axis.

8. A display method for a sleep evaluation device, that displays a level of a sleeping state of a subject, out of a plurality of levels of the sleeping state of the subject, in a predetermined period having a plurality of unit periods on a display device with a graph along a time axis, based on a sensor signal that detects body motion of the subject output from a sensor, comprising:
receiving input of the sensor signal;
discriminating the sleeping state of the subject for each unit period, based on the sensor signal;
discriminating the level of the sleeping state of the predetermined period which consists of continuous unit periods, based on a sleeping state discrimination result for each unit period, providing a continuous number of the sleeping state discrimination results and a ratio of a number of unit periods having the sleeping state discrimination results to a total number of the unit periods within the predetermined period, and based on a stored determination value for each of the plurality of levels of the sleeping state;

deciding a display mode for each predetermined period, according to the level of the sleeping state of the predetermined period; and generating display data that represents the level of the sleeping state of the predetermined period with the display mode.

* * * * *